United States Patent [19]
Pinto et al.

[11] B 3,993,585
[45] Nov. 23, 1976

[54] ELEVATED HUMAN LIPIDS CONTROL

[75] Inventors: Joseph Diago Pinto, Hollywood Hills; Raj Kumar, Pembroke Pines, both of Fla.

[73] Assignee: American Cyanamid Company, Stamford, Conn.

[22] Filed: Jan. 27, 1975

[21] Appl. No.: 544,476

[44] Published under the second Trial Voluntary Protest Program on February 24, 1976 as document No. B 544,476.

[52] U.S. Cl. .............................. 252/408; 23/230 B
[51] Int. Cl.² ........................................ G01N 33/16
[58] Field of Search .................. 252/408; 23/230 B

[56] References Cited
UNITED STATES PATENTS

| | | | |
|---|---|---|---|
| 3,736,263 | 5/1973 | Parekh et al. | 252/408 |
| 3,891,573 | 6/1975 | Stary et al. | 252/408 |

*Primary Examiner*—Leland A. Sebastian
*Attorney, Agent, or Firm*—Charles F. Costello, Jr.; J. Richards

[57] ABSTRACT

A human lipids control serum comprising normal human serum to which has been added a human plasma fraction high in lipids for use as a control in assay for lipids.

5 Claims, No Drawings

3,993,585

ELEVATED HUMAN LIPIDS CONTROL

BACKGROUND OF THE INVENTION

The present invention is in the field of diagnostics and is particularly concerned with lipid assays and an improved human lipids control serum possessing higher than normal concentrations of lipids, such as triglycerides, cholesterol, phospholipids, total lipids, glycerol and non-esterified fatty acids, all obtained from a lipid rich fraction of human plasma. The present invention involves a normal human serum carrier to which has been added a human plasma fraction such as Cohn Fraction III-2,1, rich in lipids to give an all human control serum possessing elevated concentrations of lipids.

Lyophilized elevated lipid control sera comprising human serum selected from individuals known to possess elevated concentrations of lipids for use as a control in assays for lipids is known and currently available.[1] However, such a sera is inconvenient and expensive to obtain and not as readily available as desired since it depends solely upon the availability of and accessability to individuals possessing elevated concentrations of lipids. The present invention overcomes these disadvantages.

[1] e.g., Elevated Lipids Control Serum, Lederle Diagnostics, American Cyanamid Company, Pearl River, New York.

It is known that certain fractions of human plasma are rich in lipids such as Cohn Fraction III, and similar fractions, Cohn, E. J. et al., J. Amer. Chem. Soc. Vol. 68, pp. 459–475 (March, 1946). Cohn Fraction III is obtained in the processing of whole blood to plasma as a precipitate formed during alcoholic extraction, Cohn, et al. supra. The lipid constituents of Cohn Fraction III vary from batch to batch but fractions having arbitrarily set minimum values for constituents of importance to the establishment of a control have been determined to be satisfactory as starting materials.

U.S. Pat. No. 3,751,381 discloses a non-lyophilized serum lipid assay standard containing the lipid rich Cohn Fraction III in conjunction with bovine serum albumin to enhance the stability of the protein constituents in the serum and a yellow dye to give a color more closely approximating that of the lipid rich portion of fresh serum. The U.S. Pat. No. 3,751,381 patent points out that the reference standard disclosed therein is not suitable for reduction to the lyophilized state as it has been found that lyophilization greatly reduces the quality of the standard which is manifested by reduced recoverable lipoproteins and by increased turbidity of the reconstituted material.

U.S. Pat. No. 3,260,648 discloses a lyophilized standard composition to be reconstituted when needed for use in the determination of total cholesterol levels in human blood plasma comprising lyophilized, processed human blood plasma, a predetermined quantity of total cholesterol in the free form or as an ester derived from unknown sources and a necessary solubilizing agent to help dissolve the cholesterol upon reconstitution.

U.S. Pat. No. 3,682,835 discloses an aqueous blood serum control standard for use in the analysis of blood serum comprising defibrinated plasma which has been treated with a strong acid cation exchange resin to reduce the alkali and alkaline earth metal cation level and from which the lipoprotein component has been removed by extraction with a fat solvent. Cholesterol is said to be illustrative of a blood serum component which can be added to the aqueous liquid for use as a control.

U.S. Pat. No. 3,764,556 discloses a lipid control made up of triglyceride and cholesterol rich fractions from chicken eggs and outdated human plasma, and certain fractions of horse or bovine sera.

None of the above art is concerned with an all human elevated lipid control serum as disclosed herein.

SUMMARY OF THE INVENTION

The present invention covers the method of making an all human elevated lipids control serum as disclosed herein, in both its liquid suspension and lyophilized forms, the elevated lipids control serum so prepared, and the method of using the elevated lipids control serum as a control in assays for lipids.

The basic carrier material for the elevated lipid control serum of this invention is human plasma obtained from blood bands and/or plasmapheresis centers containing the usual anticoagulants. The carrier material can be plasma collected in all authorized anticoagulants such as adenine-citrate-dextrose, citrate-phosphate-dextrose, sodium citrate and sodium heparin. The plasma is pooled and defibrinated. The lipid rich material to be added to the carrier material, Cohn Fraction III-2,1 is derived from venous plasma. The elevated lipid control serum is prepared by the addition of an appropriate amount of Cohn Fraction III-2,1 to the pooled and fibrinogen free serum.

Basically, the all human elevated lipid control serum of this invention is made by adding together two components, i.e., the carrier and the lipid rich fraction, both of which can be derived from normal human plasma containing anticoagulants. The carrier can be prepared by adding an anion exchange resin such as Dowex 1-X-4 in its chloride form to normal human plasma to remove citrate. The supernatant is then heated to 37°C. to precipitate fibrin and in this process the plasma is converted to serum. The serum is concentrated by dialysis against polyethylene glycol 6000 placed inside a dialysis bag. A 20–30% reduction in volume of the serum is desirable. The lipid rich fraction, Cohn Fraction III-2,1, can be obtained as shown in Example 2 herein. A 20 gram percent solution of wet Cohn Fraction III-2,1 is prepared in phosphate buffer. The carrier serum prepared above and the Cohn Fraction III-2,1 are mixed in various proportions to give a control containing any concentration of lipids desirable.

Intrinsic lipid values of Cohn Fraction III-2,1 have been shown to be as follows: 3 grams of Cohn Fraction III-2,1 dissolved in 100 ml. of phosphate buffer, pH 8.1, and filtered prior to assay, assayed cholesterol 61 mg./100 ml. and triglycerides 87 mg./100 ml.; and 20 grams of Cohn Fraction III-2,1 dissolved in 100 ml. of phosphate buffer, pH 7.4, and filtered prior to assay, assayed cholesterol 372 mg./100 ml. and triglycerides 434 mg./100 ml. As to the quantity of Cohn Fraction to be added to plasma, baseline assays are done on both plasma and freshly dissolved Cohn Fraction III-2,1 prior to blending. Target ranges for concentration of lipid constituents are determined by the production protocol for a particular product.

Cohn Fraction III-2,1 is a known material derived from a modification of one of the original fractionation schemes derived by Cohn and his associates. In addition to Cohn Fraction III-2,1, other fractions such as Cohn Fraction III are well as sub-fractions may also be suitable.

The present invention is an outgrowth of an investigation into the use of fractions discarded during the processing of plasma for production of albumin and gamma globulin. For example, in the preparation of tetanus immune globulin (human) from venous plasma using a modified Cohn fractionation scheme there is obtained a fraction designated Cohn Fraction III-2,1 which was formally discarded. Cohn Fraction III-2,1 contains a high proportion of lipids. The present invention utilizes this Cohn Fraction III-2,1 with its high liqid content, by adding it to a pool of normal human serum to bring the levels of lipids, e.g., cholesterol, triglycerides and phospholipids, into the abnormally elevated range to obtain an elevated lipids control for use in lipid assays.

Advantages of this invention include the fact that all of the lipids are derived exclusively from human sources; the use of Dowex 1-X-4 resin to remove the citrate ions thus freeing calcium ion for participation in the fibrin clotting mechanism; clot formation accomplished at a relatively low temperature and short time interval which obviates significant removal or destruction of other blood constituents; the use of relatively mild conditions of dialysis to concentrate the serum and to significantly reduce glucose and some electrolyte concentration such as sodium; the stability of the lyophilized product, shown stable for at least two years at 4°–8°C., and its rapid reconstitution in water; and lastly, a much cheaper product to produce than the alternative which is the collection of serum from hyperlipidemic donors.

The human lipids control serum product of this invention is intended to be used primarily as a biological control in clinical determinations for triglycerides, cholesterol, glycerol, phospholipids, total lipids and nonesterified fatty acids, mainly in hospitals, commercial clinical laboratories and in medical centers. In order for the analyst to have confidence in the results of tests done on patient's serum for one of these components it is necessary to test a biological control that resembles, as closely as possible, the patient's serum. It is contemplated that the human lipids control serum, with component values included in a package, will serve to assure the analyst that his assay procedures are functioning correctly and that his technique is suitable. The product of this invention is to serve as a quality control for assay procedures and is not intended as a standard with which assay levels are determined.

DETAILED DESCRIPTION OF THE INVENTION

Fibrinogen free serum is obtained by treating pooled normal plasma containing anticoagulant agents such as adenine-citrate-dextrose (ACD) or citrate-phosphate-dextrose (CPD) or sodium citrate solution with an ion exchange resin such as Dowex 1-X-4 to remove the citrate ions. This frees the calcium ions to participate in the fibrin clotting mechanism. The plasma is then heated to 37°C. to 40°C. (preferably 37°C.) for a time, usually 30 minutes, sufficient to produce the fibrin clot. The clot is removed leaving serum. Since originally dilution of the plasma with anticoagulant solution lowers the normal concentration of lipid components this fibrin free serum is dialyzed against polyethylene glycol 6000 to concentrate the fibrin free serum to its original level.

The Cohn Fraction III-2,1 is derived from treatment of venous plasma through a series of alcohol fractionations and buffer suspensions as shown in Example 2 herein. The Cohn Fraction III-2,1 containing high lipid levels, is then mixed with the fibrin free serum at predetermined concentration and lyophilized to produce the elevated lipid serum of this invention.

In order to show the efficacy of the elevated lipid serum control prepared according to the procedure set forth herein, a portion of Dowex 1-X-4 resin was added to normal plasma containing the anticoagulant ACD. After stirring and allowing the resin to settle the plasma was recovered and incubated at about 37°C. for 30 minutes. The clot which formed was removed by filtration and the serum was recovered. This serum was placed outside a dialysis bag and dialyzed against 25 grams of polyethylene glycol 6000, placed inside the dialysis bag and kept at 4°C. for approximately 2–3 hours. The volume of serum was reduced about 35%. This serum was diluted to its original volume with a 20% solution of Cohn Fraction III-2,1 in 0.1M phosphate buffer pH 7.0–7.4, mixed, placed in bottles at 5 ml. per bottle and lyophilized. The lyophilized samples were reconstituted with 3 ml. of water and assayed for cholesterol and triglycerides. A portion of normal serum containing the anticoagulant CPD was treated and assayed in the same manner.

The results appear in Table I.

TABLE I

| Sample | Cholesterol Optical Density | mg % | Triglycerides Optical Density | mg% |
|---|---|---|---|---|
| Standard | 0.36 | — | 0.27 | — |
| Elevated Lipid Control* | 0.39 | 324 | 0.27 | 300 |
| ACD Serum | 0.49 | 408 | 0.34 | 378 |
| CPd Serum | 0.55 | 458 | 0.49 | 544 |

*Normal Clinical Chemistry Control Serum, human serum containing those constituents usually found in serum in "normal" concentrations, including, cholesterol and triglycerides, for use as a control, Lederle Diagnostics, American Cyanamid Company, Pearl River, New York.

The invention will be further described in conjunction with the following non-limiting examples.

EXAMPLE 1

Conversion of Normal Plasma Containing Anticoagulants ACD or CPD to Serum

Dowex 1-X-4 resin in the chloride form (100–200 mesh) is washed three times with four times its volume of distilled water and collected by filtration on a Buchner funnel. A 20 gm. portion of wet resin is added per 100 ml. of anticoagulant containing plasma and mixed for 5 minutes. The resin is allowed to settle and the supernatant plasma is collected by decantation. This plasma is heated at 37°C. for 30 minutes. The fibrin clot which forms is removed by passing the suspension through cheesecloth. The serum which is collected has originally been diluted about 15% by the addition of anticoagulants. This serum is placed outside a polyethylene dialysis bag containing 20 gm. of dry polyethylene glycol per 100 ml. of serum and dialyzed for 2 hours. The volume of the serum is reduced by about 30%.

EXAMPLE 2

Preparation of Cohn Fraction III-2,1

Absolute methanol is added to human venous plasma to a concentration of 8–10% at 0° to 3°C. and centrifuged. The methanol concentration of the supernatant is raised to 25% at −5° to −7°C. and then centrifuged. The precipitate is suspended in phosphate buffer, pH 7.2 to 7.4, at 0° to −6°C., the methanol concentration is adjusted to 20% and centrifuged. The precipitate is suspended in acetate buffer, pH 5.0 to 5.2, at 0° to −6°C., the methanol concentration is adjusted to 14 to 17% and centrifuged. The resulting precipitate is designated as Cohn Fraction III-2,1.

EXAMPLE 3

Preparation of Elevated Lipid Control Serum

A 65 ml. portion of dialyzed serum, prepared as described in Example 1 is diluted to 100 ml. with a 20% solution of Cohn Fraction III-2,1 in phosphate buffer and mixed. This solution is divided into 5 ml. quantities and lyophilized. Cholesterol and triglyceride assays are performed using standard colorimetric techniques. The elevated lipid control has a cholesterol content of 458 gm% based on an optical density of 0.55 and a triglyceride content of 544 gm% based on an optical density of 0.49.

The elevated lipid control serum of this invention is to be supplied as a lyophilized control serum, freeze dried for maximum stability. In use, using a volumetric pipette, 5.0 ml. of distilled water is added to a vial of dried serum, swirled gently to mix and allowed 10–15 minutes for complete reconstitution. The mixture should be mixed well before removing a portion for assay and is analyzed in the same manner as an unknown specimen including all steps in the procedures.

We claim:

1. The method of making an all human elevated lipid control serum for use as a control in assays for lipids which comprises the steps of:
   a. treating normal anticoagulant containing plasma with an ion exchange resin to effect clotting;
   b. heating the supernatant plasma at 30° to 40°C. for 15 to 45 minutes to precipitate the clot;
   c. dialyzing the recovered serum against polyethylene glycol to concentrate the serum; and
   d. adding a 10% to 30% solution of Cohn Fraction III-2,1 in 0.1M, pH 7.0–7.4 phosphate buffer to the dialyzed serum in a proportion which provides a final product having concentrations of lipid components in an elevated range.

2. The method of claim 1 which includes the additional steps of lyophilizing the final product.

3. A human elevated lipid control serum for use as a control in assays for lipids prepared by the method of claim 1.

4. A human elevated lipid control serum for use as a control in assays for lipids prepared by the method of claim 2.

5. In the performance of diagnostic tests for the determination of lipid levels the improvement comprising employing in said tests the control prepared by the method of claim 2 which has been reconstituted with water.

* * * * *